United States Patent
Ohshima et al.

(10) Patent No.: US 7,551,722 B2
(45) Date of Patent: Jun. 23, 2009

(54) X-RAY TARGET AND APPARATUSES USING THE SAME

(75) Inventors: Ken-ichi Ohshima, Tsukuba (JP); Jinpei Harada, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 188 days.

(21) Appl. No.: 11/547,801

(22) PCT Filed: Apr. 8, 2005

(86) PCT No.: PCT/JP2005/007279

§ 371 (c)(1), (2), (4) Date: Oct. 6, 2006

(87) PCT Pub. No.: WO2005/098871

PCT Pub. Date: Oct. 20, 2005

(65) Prior Publication Data

US 2007/0248215 A1 Oct. 25, 2007

(30) Foreign Application Priority Data

Apr. 8, 2004 (JP) ............................. 2004-114704

(51) Int. Cl.
*H01J 35/08* (2006.01)
*G21K 7/00* (2006.01)

(52) U.S. Cl. ........................................ 378/143; 378/43

(58) Field of Classification Search .................. 378/42, 378/43, 44, 143, 144, 119, 138
See application file for complete search history.

(56) References Cited

U.S. PATENT DOCUMENTS 6,850,598 B1 * 2/2005 Fryda et al. ................. 378/161

(Continued)

FOREIGN PATENT DOCUMENTS

JP 62-276737 A 12/1987

(Continued)

OTHER PUBLICATIONS

Translation of International Preliminary Report on Patentability mailed Mar. 1, 2007 of International Application No. PCT/JP2005/007279.

(Continued)

*Primary Examiner*—Irakli Kiknadze
(74) *Attorney, Agent, or Firm*—Westerman, Hattori, Daniels & Adrian, LLP.

(57) ABSTRACT

Disclosed are an X-ray target having a micro focus size and capable of producing X-rays of high intensity, and apparatuses using such an X-ray target. The X-ray target (1) has a structure in which a first cap layer (21), a target layer (22), and a second cap layer (23) are successively laminated, wherein the first and second cap layers (21 and 23) are each composed of a material which is lower in electron beam absorptivity than that of which the target layer (22) is composed. An X-ray generator using the X-ray target (1) can generate highly intense and nanofocus (several nm) X-rays (17). Using the X-ray generator, an X-ray microscope allows obtaining a high resolution transmission image, an X-ray diffraction apparatus allows obtaining an X-ray diffraction image of a very small area, and a fluorescent X-ray analysis apparatus allows making the fluorescent X-ray analysis of a minute area.

17 Claims, 12 Drawing Sheets

U.S. PATENT DOCUMENTS

2003/0086533 A1* 5/2003 Janik et al. .................. 378/138
2006/0133576 A1* 6/2006 Wilkins et al. .............. 378/124

FOREIGN PATENT DOCUMENTS

| | | |
|---|---|---|
| JP | 5-74392 A | 3/1993 |
| JP | 6-188092 A | 7/1994 |
| JP | 11-258400 A | 9/1999 |
| JP | 2002-313266 A | 10/2002 |

OTHER PUBLICATIONS

J. Harada et al.; "Ultra-fine Radiography based on Micro X-ray Source"; Japan Society of Photography, vol. 65, No. 7, pp. 495-500, 2002.

S. W. Wilkins et al.; "Phase-contrast imaging using polychromatic hard X-rays"; Nature, vol. 384, pp. 335-338, Nov. 28, 1996.

International search report of PCT/JP2005/007279, date of mailing Aug. 2, 2005.

* cited by examiner

X-RAY TARGET AND APPARATUSES USING THE SAME

TECHNICAL FIELD

The present invention relates to an X-ray target having a nano focus size and capable of producing X-rays of high intensity, and apparatuses using such an X-ray target.

BACKGROUND ART

X-rays can be used to make a detailed nondestructive examination of the internal structure of a material. For example, observation by transmission X-ray imaging has extensively been applied to such as the diagnosis of a living body in medical and pharmaceutical fields, the evaluation of various industrial products and an apparatus for the inspection of pieces of luggage in an airport. Other than those utilizing synchrotron radiation, the X-ray sources currently used include an X-ray tube based on the method of striking accelerated electrons on a metallic target in vacuum to emit X-rays from the target. As the X-ray source that can be obtained by this method has a size of several μm generally, the resolution obtainable by the X-ray radiography has remained in several μm, too, which has not been satisfactory.

It was reported by the present inventors that in around 1973, an X-ray photograph was taken of an ant with a microfocus X-ray source of 3 μm diameter to observe its body hair and blood vessels (see: Jinpei Harada and Masaru Kuribayashi, "High-Definition Images by Micro-focus X-ray Source", Japan Society of Photography, vol. 65, No. 7, pp. 495-500, 2002). In this photographing, the X-ray target used was made of gold (Au) and had a thickness of 2 μm. While the X-ray radiographic imaging contrast has been said to be due to the scattering and absorption of X-rays, it is pointed out that the use of a microfocus X-ray source allows a phase-contrast image to be included and therefore to capture the contours of an object if it is such as a hair which is low in density and very small in thickness (see: S. W. Wilkins and four others, "Phase-contrast imaging using polychromatic hard X-ray", Nature, vol. 384, pp. 335-338, 1996).

FIG. 12 is a diagram schematically illustrating a conventional X-ray source. In the Figure, applying an electron beam 100 to a target thin film 101 of thickness t is shown to generate X-rays 102. In this case, electrons 103 diffuse into the target thin film 101 with a diffusion length L.

X-rays are also used in the inspection of a semiconductor device, especially an ultra LSI (large Scale Integrated Circuit) by elemental analysis or X-ray photoelectron spectroscopy (XPS) with characteristic X-rays or fluorescent X-rays. For example, the Japanese laid open patent application JP H05-45306 A discloses a method for X-ray analysis in which X-rays radiated from a rotating target as the X-ray source are passed through a fine glass tube to generate a fine X-ray beam of 5 μm in diameter on a specimen. In this method, numbers of fine glass tubes are used to enhance the intensity of X-rays. For this reason, different focus sizes are apt to be produced from different fine glass tubes, and the arrangement is unsuitable for X-ray radiographic or transmission imaging. Further, there are also limits in machining such a fine glass tube. However, the requirement indeed exists for an X-ray source of still finer focus size to meet with semiconductor elements having a minimum feature size of 90 nm or 60 nm.

However, while reducing the focus size of a conventional X-ray source as shown in FIG. 12 requires reducing the spot size of an electron beam and increasing the density of electrons in the electron beam for irradiation, the problem arises that if this is done, electrons forming the beam still then diffuse within the X-ray target and fail to give rise to a fine focus X-ray source. Also, if the density of electrons is raised in the beam for irradiation, the problem emerges that this will cause the X-ray target material to be heated to a molten state and then to a sublimed or evaporated state, and will damage the target thin film 101.

DISCLOSURE OF THE INVENTION

With these problems taken into account, it is an object of the present invention to provide a nano focus X-ray target capable of generating X-rays of a high intensity and an apparatus using such an X-ray target.

In order to achieve the object mentioned above, the X-ray target of the present invention is characterized in that it has a structure in which a first cap layer, a target layer and a second cap layer are successively laminated, wherein said first and second cap layers are each composed of a material which is lower in electron beam absorptivity than that of which said target layer is composed.

There is also provided in accordance with the present invention in another construction thereof an X-ray target, characterized in that it is made of a target section composed of a material capable of generating characteristic X-rays and a film with which said target section is covered, wherein said film is composed of a material which is lower in electron beam absorptivity than that of which said target section is composed.

In an X-ray target so constructed as mentioned above, said target layer or section is preferably composed of a material capable of generating characteristic X-rays of a wavelength ranging between 0.3 and 10 Å.

Said first and second cap layers or said film with which said target section is covered is preferably composed of a material selected from the group which consists of B, C, SiC and $B_4C$.

With an X-ray target so constructed as mentioned above, the first and second cap layers which are lower in electron beam absorptivity than the target layer are harder to heat than the target layer. Therefore, if the target layer is heated and molten by the convergent electron beam, the molten target layer 22 will be confined within the first and second cap layers and thereby be prevented from its sublimation or vaporization. As a consequence, the intensity of an electron beam towards the X-ray target can be increased to raise the intensity or brightness of the X-ray source. Further, making the target layer thinner can also make the X-ray source three-dimensionally smaller in focus size.

Thus, according to the X-ray target of the present invention, the emission efficiency of X-rays can be improved since the convergent electron beam can be narrowed to the size of the target layer or section and its intensity can be raised for application to the X-ray target. As a consequence, it is possible to make the focus size of the electron beam smaller according to the size of the target layer or the target section. For example, the focus size can be reduced to the nm order. Therefore, it becomes possible to provide a nano focus X-ray target.

In the X-ray target so constructed as mentioned above, the target layer or section is preferably in the form of a line or an elliptical shape. Accordingly, even if the X-ray target is irradiated with an electron beam expanded in cross sectional area, the size of the X-ray focus size which is determined by the size of the target layer or section in the form of a line or an elliptical shape is no further increased. As a consequence, nano focus X-rays can be generated efficiently. Since the density of an electron beam can be increased so that the target layer or section may even be molten, the X-ray brightness or intensity can further be increased.

In the X-ray target so constructed as mentioned above, such target layers or sections as aforesaid are preferably arranged in the form of a matrix. Also, said target layers or sections arranged in the form of a matrix are preferably linear and/or elliptical in shape, and identical or dissimilar in size.

With the X-ray target so constructed as mentioned above, the individual target layer or section may be exchanged by a mechanical operation thereof or changing the position of irradiation with an electron beam and used for a selected time period or the like. This eliminates the need to exchange the X-ray target upon breaking the vacuum of a vacuum chamber, thereby enhancing its convenience. Also, the size of a target layer or target section as an individual matrix element may make the convergent electron beam having a desired focus size. Further, with the individual matrix elements varying in size, selecting one matrix element from another allows the focus size of a convergent electron beam to be varied and hence X-rays of different micro focus sizes to be generated.

The X-ray target so constructed as mentioned above is preferably further provided with a support block with which said X-target is held. According to this construction, the X-ray target which is mechanically held by the support block is prevented from bending. Also, the heat is effectively dissipated from the X-ray target by the support block.

In accordance with the present invention there is also provided in another form of implementation thereof an X-ray apparatus including an X-ray source made of an electron beam generating section and an X-ray target, characterized in that: said X-ray target has a structure in which a first cap layer, a target layer and a second cap layer are successively laminated, or is made of a target section composed of a material capable of generating characteristic X-rays and a film with which said target section is covered, wherein said first and second cap layers are each, or said film is, composed of a material which is lower in electron beam absorptivity than that of which said target layer or said target section is composed, whereby irradiating said X-ray target with a convergent electron beam generated by said electron beam generating section causes said X-ray target to generate microfocus X-rays.

With the X-ray apparatus so constructed as mentioned above, the emission efficiency of X-rays can be improved since the convergent electron beam can be narrowed to the size of the target layer or section and its intensity can be raised for application to the X-ray target. It becomes possible, therefore, to generate nano focus X-rays of high intensity.

In the X-ray apparatus so constructed as mentioned above, it is preferable that said electron beam generating section includes an electronic lens, that said X-ray target be disposed with an inclination to the convergent electron beam generated by said electron beam generating section, and that said convergent electron beam be similar in shape to said target layer or section in said X-ray target. The shape is preferably in the form of a line or elliptical shape. With the X-ray apparatus so constructed, since an X-ray target larger in area can be irradiated with a convergent electron beam, the brightness or intensities of X-rays can further be increased by reducing the focus size further. It follows, therefore, that the nano focus X-rays of high intensity can be obtained.

The X-ray apparatus so constructed as mentioned above is preferably an X-ray diffraction apparatus further provided with an observatory sample holder section and an X-ray detecting means. So constructed, an X-ray diffraction apparatus can be provided that is capable of measuring the X-ray diffraction of a very small area with a highly intense and nano focus X-ray source.

The X-ray apparatus so constructed as mentioned above is also preferably a fluorescent X-ray analysis apparatus further provided with an observatory sample holder section and an X-ray detecting means. So constructed, the fluorescent X-ray analysis apparatus can be provided that is capable of making the fluorescent X-ray analysis of a very small area with a highly intense and nano focus X-ray source.

The X-ray apparatus so constructed as mentioned above is preferably further provided with an X-ray optical element. This feature makes it possible to irradiate an observable object efficiently with X-rays of a particular wavelength selected from a microfocus (or nanofocus) and highly intense X-ray source.

In accordance with the present invention there is also provided in another form of implementation thereof an X-ray microscope including an electron beam generating section, an X-ray target, an observational sample holder section for an observable object, and an X-ray detecting means, characterized in that said X-ray target has a structure in which a first cap layer, a target layer and a second cap layer are successively laminated, or is made of a target section composed of a material capable of generating characteristic X-rays and a film with which said target layer is covered, wherein said first and second cap layers are each, or said film is, composed of a material which is lower in electron beam absorptivity than that of which said target layer is composed, whereby irradiating said X-ray target with a convergent electron beam generated by said electron beam generating section causes said X-ray target to generate microfocus X-rays, and said microfocus X-rays are used as divergent X-rays to obtain a transmission X-ray image of said observable object.

So constructed as mentioned above, the X-ray microscope can be provided that is capable of obtaining an X-ray transmission image in a high resolution with divergent X-rays from microfocus X-rays generated by narrowing a convergent electron beam to the size of a target layer or section and raising its intensity.

In the X-ray microscope so constructed as mentioned above, it is preferable that said electron beam generating section comprises an electronic lens, that said X-ray target be disposed with an inclination to the convergent electron beam generated by said electron beam generating section, and that said convergent electron beam is similar in shape to said target layer or section in said X-ray target. Also, said shape is preferably in the form of a line or elliptical shape. So constructed, the X-ray microscope can be provided in which the intensity of microfocus X-rays is further increased.

Said transmission X-ray image preferably includes a contrast by phase contrast. This feature makes it possible to provide an X-ray microscope whereby there can be observed not only an absorption image of an observable object but also its phase contrast. Said X-ray detecting means is preferably an image sensor and provided with an image processing means for said image sensor. This feature makes it possible to provide the X-ray microscope that can process a variety of images and is therefore highly convenient.

BEST MODES FOR CARRYING OUT THE INVENTION

Figure 1:
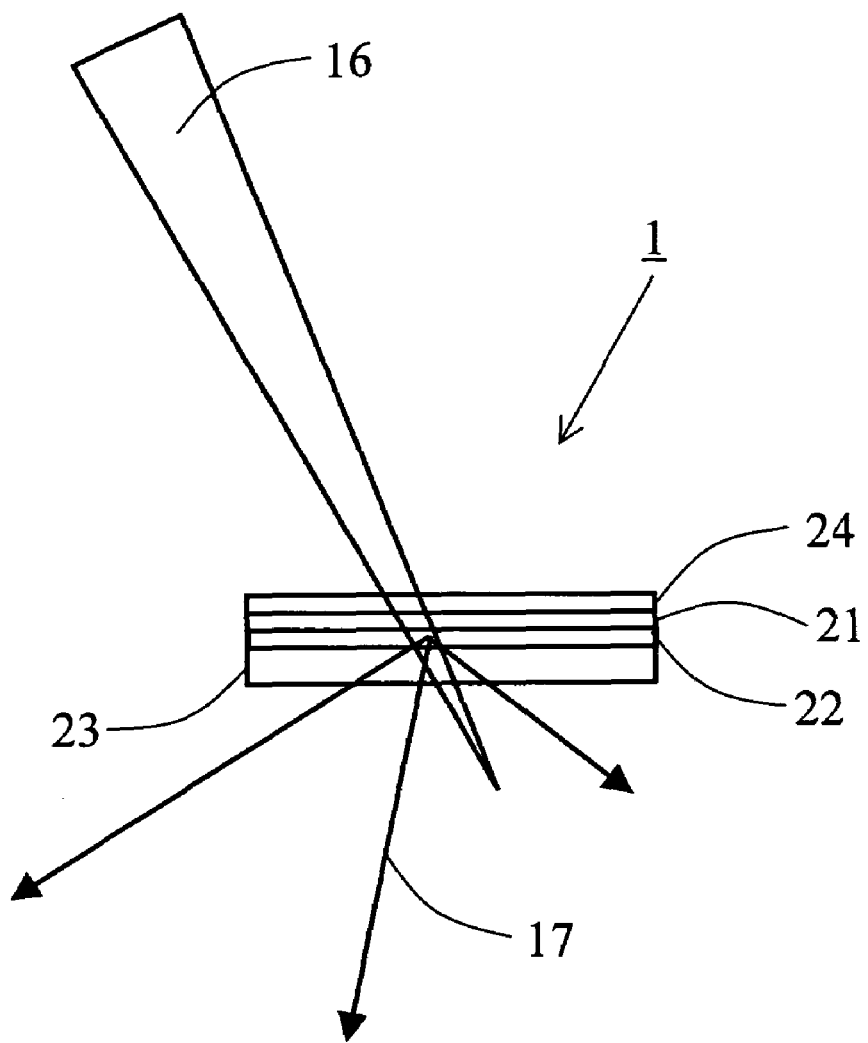
FIG. 1 is a cross sectional diagram illustrating the structure of an X-ray target according to a first form of implementation of the present invention.

The present invention will better be understood from the following detailed description and the drawings attached hereto showing certain illustrative forms of implementation of the present invention. In this connection, it should be noted that such forms of implementation illustrated in the accompanying drawings hereof are intended in no way to limit the present invention but to facilitate an explanation and understanding thereof. In the Figures, the same reference numerals are used to designate the same or corresponding parts.

First Form of Implementation

FIG. 1 is a cross sectional diagram illustrating the structure of an X-ray target according to a first form of implementation of the present invention. As shown in the FIG. 1, the X-ray target designated by reference numeral 1 comprises, from the above from which a convergent electron beam 16 is applied, a first cap layer 21, a target layer 22 on which the convergent electron beam 16 is focused to generate X-rays, and a layer 23 consisting of a second cap layer. This X-ray target 1 operates as a so-called transmission type X-ray target which uses components transmitted downwards of the paper, of the X-rays produced at the target layer 22. The first cap layer 21, the target layer 22 where the electron beam generates X-rays, and the layer 23 made of the second cap layer may be of thickness through which the electron beam can be transmitted and so can be the X-rays generated.

Each of the first and second cap layers 21 and 23 can be one or more than one layer. Desirably, the first and second cap layers 21 and 23 are each made of a light element through which the accelerated electron beam can easily pass or a compound thereof, which is a material that is lower in electron beam absorptivity than the target layer 22. The first and second cap layers 21 and 23 may be higher in melting point than the target layer 22. It may be that the first and second cap layers 21 and 23 when irradiated with the convergent electron beam 16 is low in electron beam absorptivity or absorptance and will not rise in temperature. In other words, if the target layer 22 is high in electron beam absorptivity, the first and second cap layers 21 and 2 may each be a material that is low in electron beam absorptivity. With the X-ray target 1 so constructed, the first and second cap layers 21 and 23 that are low in electron beam absorptivity are hard to be heated while the target layer 22 that is high in electron beam absorptivity is heated.

Here, the first and second cap layer 21 and 23 may each be a layer, or a composite or multilayer of boron (B; with a melting point of about 2300° C.), carbon (C; with a melting point of about 3500° C. or more), SiC (with a melting point of about 2700° C.), $B_4C$ (with a melting point of about 2350° C.) or the like while the target layer 22 may be made of a material that is higher in electron beam absorptivity than the first and second cap layers 21 and 23. Otherwise, the target layer 22 may be of a material that is lower in melting point than the first and second cap layers 21 and 23. As such a material, use may be made of a metal such as Co, Cu, Fe, Mo or W which may be an element whose characteristic X rays have a wavelength in a range between 0.3 and 10 Å. The target layer 22 may comprise a multilayer, i.e., layers of different metals such as to generate X-rays of different wavelengths. The target layer 22 may not only be of a single metallic element but may be of a compound layer containing a special element such as to generate characteristic X-rays having a distinctive characteristic or characteristics. As such an element, for example, La (lanthanum) may be mentioned.

The first cap layer 21 irradiated with the convergent electron beam 16 may further be formed thereon with an antistatic layer 24. The antistatic layer 24 is composed of an electrically conductive layer, preferably a light element or a compound containing a light element, e.g., carbon (C).

Figure 2:
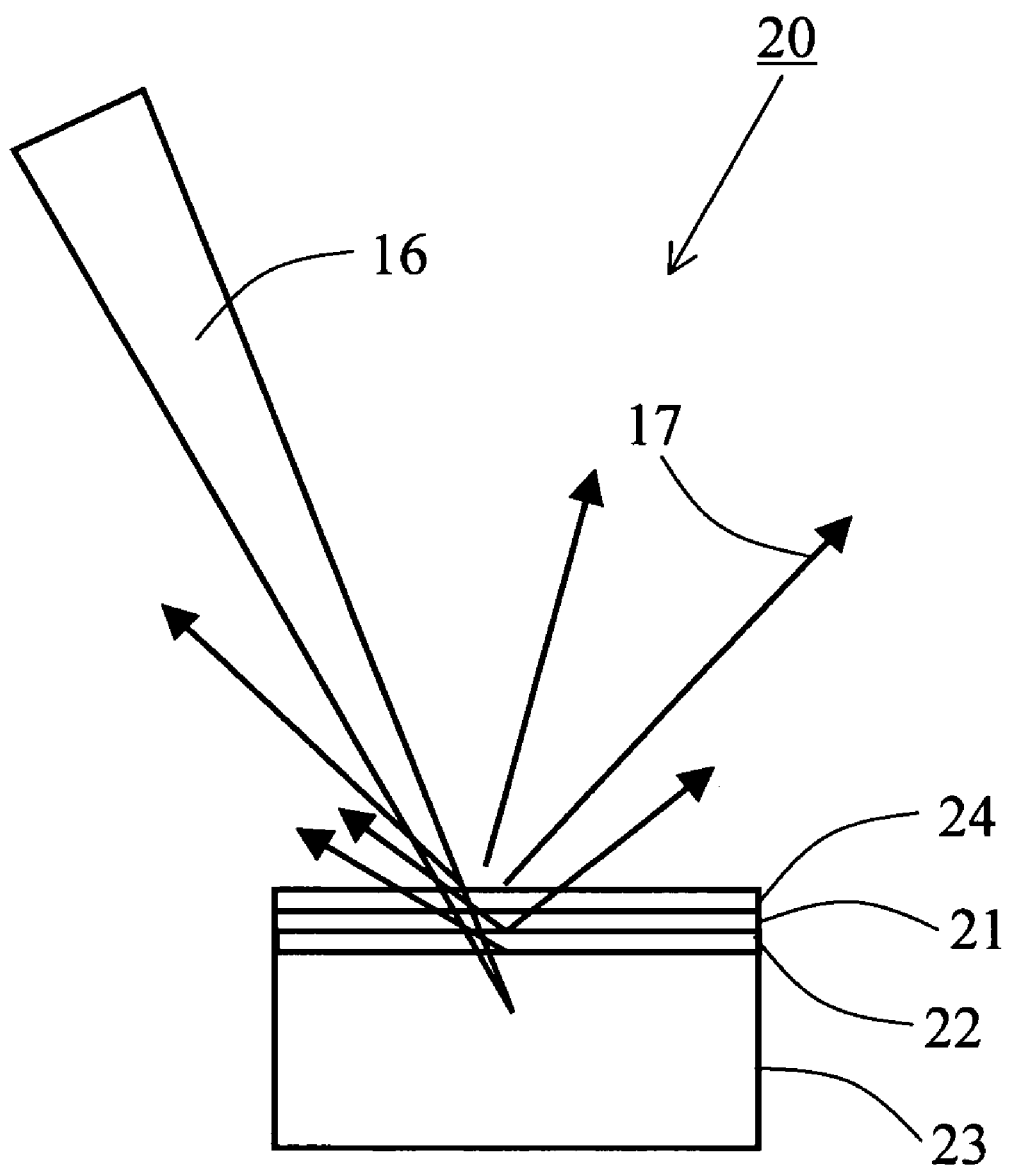
FIG. 2 is a cross sectional diagram illustrating the structure of a modification of the X-ray target according to the first form of implementation of the present invention.

Mention is next made of a modification of the X-ray target according to the first form of implementation. FIG. 2 is a cross sectional diagram illustrating the structure of such a modification of the X-ray target according to the first form of implementation. An X-ray target 20 as shown in FIG. 2 differs from the X-ray target 1 in that it is of so-called reflection type, i.e., it uses the X-rays generated on the side of the convergent electron beam 16. In case of the reflection type, the lower second cap layer 23 may be made thicker. The constructions in the other respects are the same as those of the X-ray target 1 in the first form of implementation and their repeated explanation is omitted.

Figure 3:
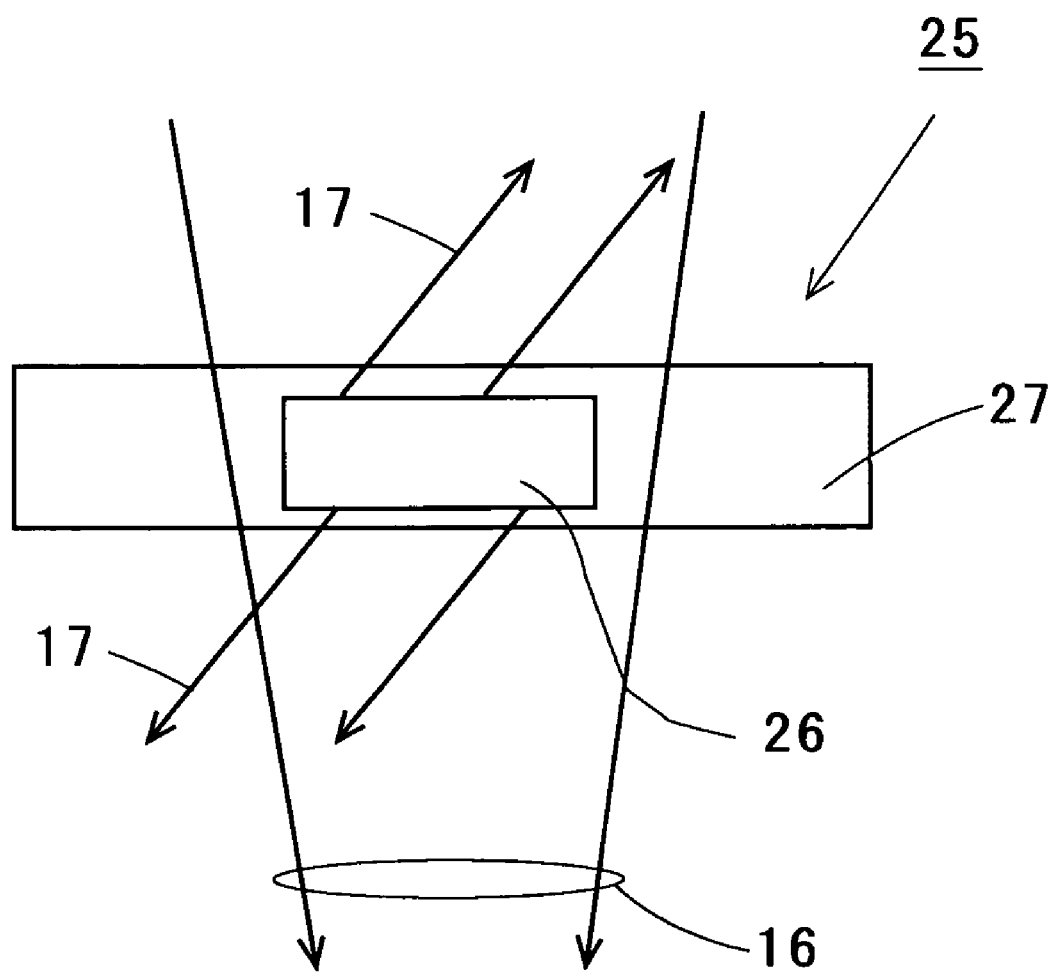
FIG. 3 is a cross sectional diagram illustrating the structure of another modification of the X-ray target according to the first form of implementation of the present invention.

An X-ray target may also be constructed as follows. An X-ray target 25 as shown in FIG. 3 comprises a target section 26 for generating X-rays 17 with a convergent electron beam 16, and a film 27 with which the target section 26 is covered entirely or enveloped. The target section 26 as is the target layer 22 in the X-ray target 1 is made of a metal such as Co, Cu, Fe, Mo or W and made in the form of a film of such a heavy element in which characteristic X-rays are of a wavelength range between 0.3 and 10 Å. On the other hand, the film 27 as are the first and second cap layers 21 and 23 in the X-ray target 1 is made of a light element through which the accelerated electron beam can easily pass or a compound thereof, which is a material that is lower in electron beam absorptivity than the target section 26. For the film 27, use may be made, for example, of a layer, or a composite or multilayer of boron (B; with a melting point of about 2300° C.), carbon (C; with a melting point of about 3500° C. or more), SiC (with a melting point of about 2700° C.), $B_4C$ (with a melting point of about 2350° C.) or the like.

Figure 4:
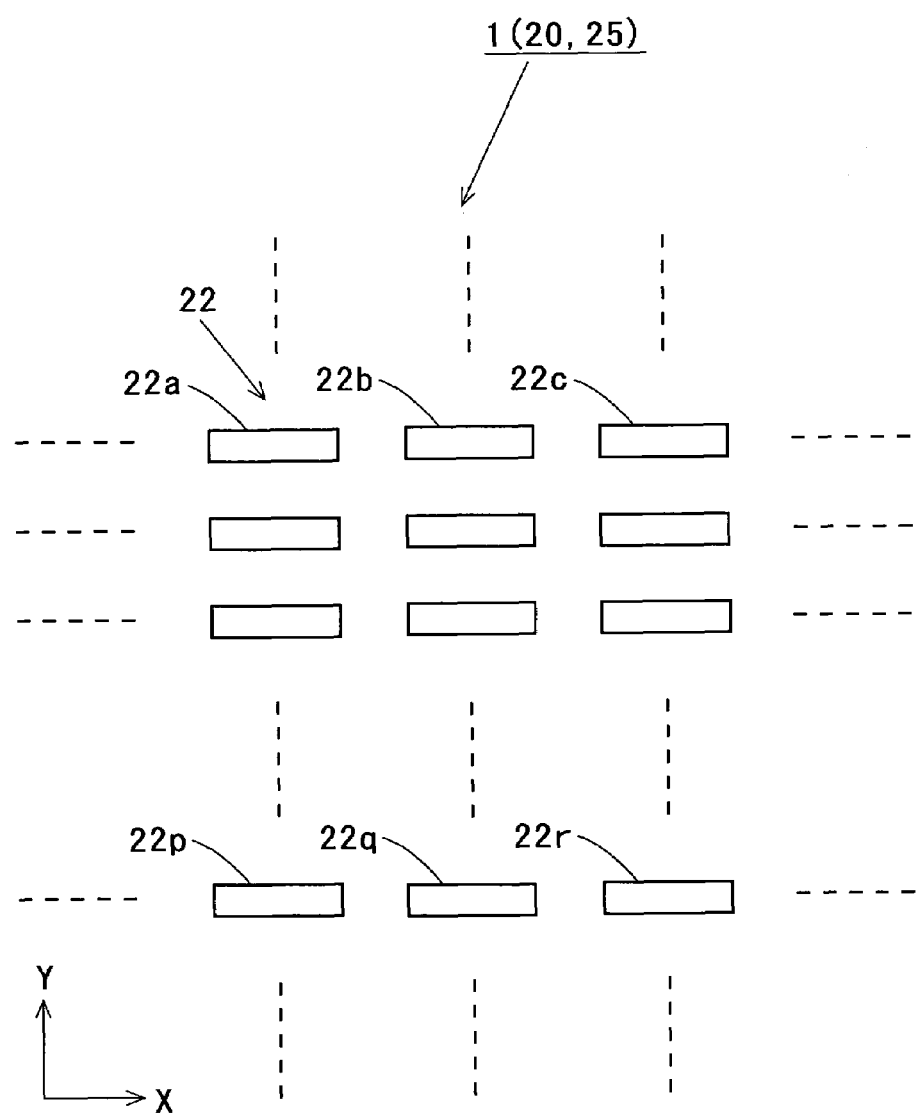
FIG. 4 is a cross sectional diagram illustrating an exemplary planar structure of the X-ray target according to the first form of implementation of the present invention.

FIG. 4 is a cross sectional diagram illustrating an exemplary planar structure of the X-ray targets 1, 20 according to the first form of implementation. In FIG. 4, while only the target layers 22 of the X-ray targets 1, 20 are shown, the target layers 22 are individually linear, and a number of them are arranged with a given spacing in X- and Y-axial directions in the form of a matrix, 22a to 22r. The target layers 22 may also be each elliptical or oval shape. They may also be each in the form of an elongated oval shape, i.e., in the form of a "koban" or small-sized Japanese gold coin containing straight lines. The term "elliptical" as it is used to refer to the shape of a target layer or section is intended to mean both oval and elongated oval shapes. While the target layers 22a to 22r are shown as being all linear in the same size, their matrix structure may be linear or elliptical shape, or a combination of lines and ellipses. They may be varied in a variety of sizes. If they are varied in size, X-rays can be generated which have their focus sizes according to their sizes.

The target layer can be replaced with another target layer as a separate matrix element, since a number of target layers 22a to 22r are arranged in the form of a matrix and embedded in the first and second cap layers 22 and 23, if the intensity of X-rays of a target layer as one matrix element is weakened. The matrix element may be exchanged and used per a selected time period or the like. Exchanging a matrix element may be performed by a mechanical operation or by changing the position of irradiation with an electron beam. Specifically, it can be done by driving a placement section holding the X-ray targets 1, 20 or changing electrically the position at which the electron beam 16 is focused. Alternatively, the individual matrix element metals of the different target layers 22 may be varied and disposed. In this case, microfocus X-rays having different wavelengths can be generated from the separate target layers 22. The shape of the target layers 22 can apply to the target sections 26 of the X-ray target 25.

A size of a target layer 22 or target section 26 as an individual matrix element may make the convergent electron beam 16 have a desired focus size. With the individual matrix elements varying in size, selecting one matrix element from another allows the focus size of the convergent electron beam 16 to be varied and hence X-rays 17 of different micro focus sizes to be generated. The X-ray targets 1, 20 can be prepared by the vapor deposition of a metal becoming target layers 22 on the whole surface of a second cap layer 23, causing the metal to be selectively etched, e.g., by photo lithography, to form a number of the target layers and then depositing thereon a first cap layer 21 to a selected thickness.

Mention is made of operations of the X-ray target according to the first form of implementation.

According to the X-ray targets 1, 20, 25, the accelerated convergent electron beam 16 when passing through the films made of a light element compound 21, 23, 27 which is low in electron beam absorptivity is not much absorbed by it, thus penetrating it while restraining the target layer 22 or the target section 26 within the film structure from being heated.

And, if the first and second cap layers 22 and 23 or the film 27 with which the target section 26 is covered entirely are made lower in electron beam absorptivity or higher in melting point than the target layer 22 or the target section 26, it is seen that if the target layer 22 or the target section 26 is heated by the convergent electron beam 16 and thereby molten, the molten target layer 22 or target section 26 can then be confined within the films of the film structure by the cap layers 22 and 23 or the film (cap layer) 27 made of a light element compound and can thereby be prevented from its sublimation or vaporization. As a consequence, the intensity of the convergent electron beam 16 can be increased to raise the intensity or brightness of the X-ray source. Further, making the target layer 22 or target section 26 thinner can also make the X-ray source three-dimensionally smaller in focus size.

According to the X-ray targets 1, 20, 25 of the first form of implementation, the emission efficiency of X-rays can be improved, since the convergent electron beam 16 can be narrowed to the size of the target layer 22 or the target section 26 and its intensity can be raised for application to the X-ray targets 1, 20, 25. As a consequence, it is possible to make the focus size of the electron beam smaller according to the size of the target layer 22 or the target section 26. For example, the focus size can be reduced to the nanometer (nm) order. Therefore, nano focus X-rays 17 can be obtained.

The Second Form of Implementation

Figure 5:
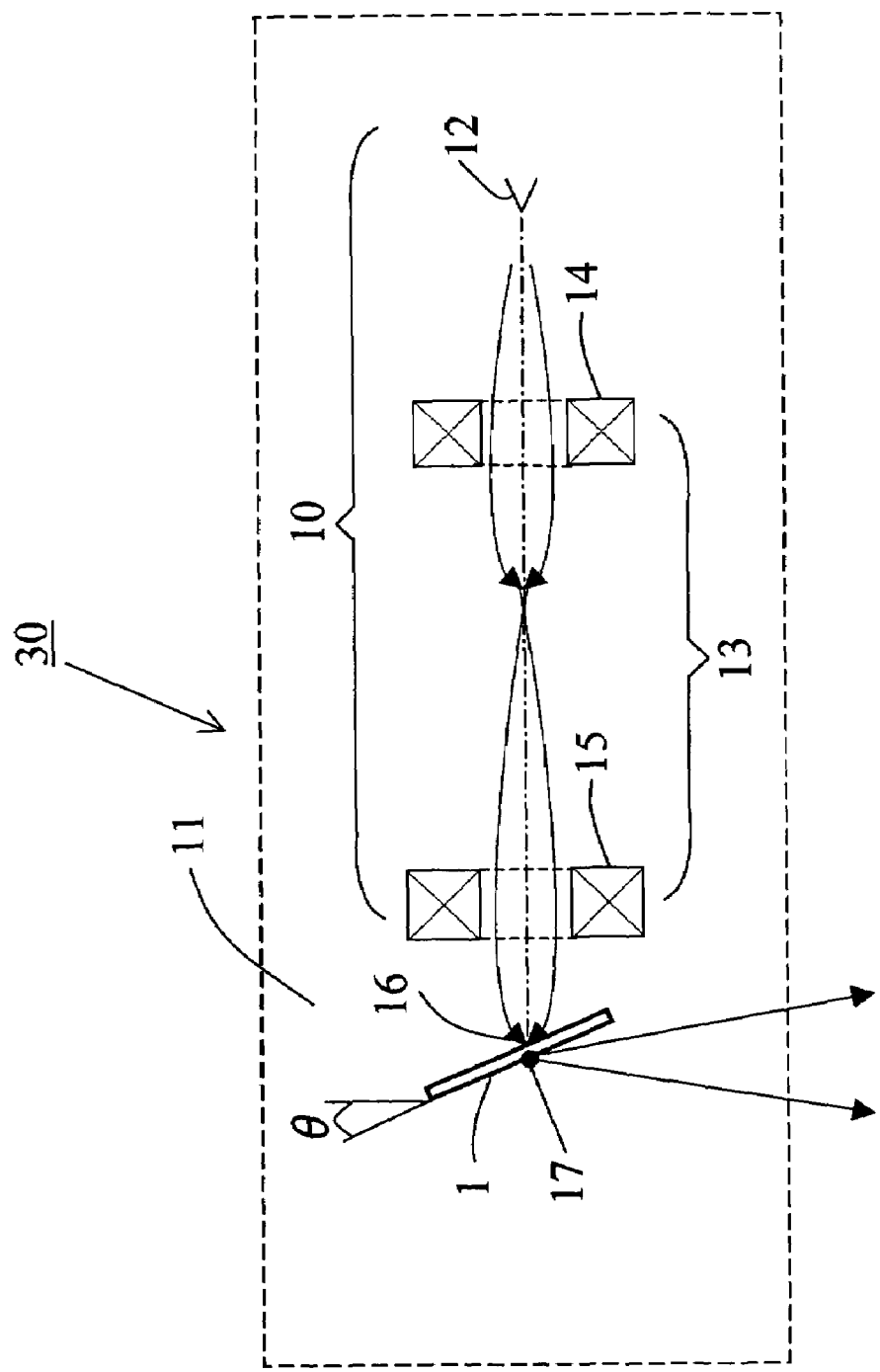
FIG. 5 is a schematic diagram illustrating the construction of an X-ray apparatus according to a second form of implementation of the present invention.

FIG. 5 is a schematic diagram illustrating the construction of an X-ray apparatus according to a second form of implementation of the present invention. In FIG. 5, an X-ray apparatus 30 is shown to be an X-ray generator with an X-ray source comprising an electron beam generating section 10 and the X-ray target 1. The electron beam generating section 10 comprises a heater 12 disposed in a vacuum chamber 11 for generating electrons and an electron beam focusing part 13 for focusing electrons emitted from the heater 12 into a convergent electron beam 16. The X-ray target 1 is irradiated with the convergent electron beam 16 to emit X-rays 17 of a nano focus size.

The electron beam focusing part 13 is made of, e.g., electronic lenses 14 and 15 in two stages and can focus the convergent electron beam 16 to around several nm. These electronic lenses may use an electrostatic lens by an electric field or a magnetic lens by a magnetic field. The X-ray target 1 is the same in construction as the X-ray target 1 according to the first form of implementation and its repeated explanation is omitted.

The X-ray target 1 is disposed to extend in a plane perpendicular to the sheet of FIG. 5 (and containing a vertical line in FIG. 5) or in a plane with an inclination to that plane. Preferably, the X-ray target 1 is disposed to extend in a plane with an angle of inclination θ to the plane perpendicular to the sheet of FIG. 5 to increase the intensity or brightness of X-rays 17 of the nano focus size. In this case, the shape of the target layer 22 in the X-ray target 1 may be in the form of a line or an ellipse with its long axis elongated. The shape of the convergent electron beam 16 may be adapted to conform to the angle and be similar to the shape of the target layer 22 in the X-ray target 1. With said angle θ being about 10 degrees, it is possible to raise the intensity of micro focus X-rays tenfold (1/sin 10°=10).

When it is mentioned that the target layer 22 and the convergent electron beam 16 are shaped in the form of a line or an elliptical shape, it should be understood that the geometrical strictness is not the intention but it is intended that they are generally so shaped.

Figure 6:
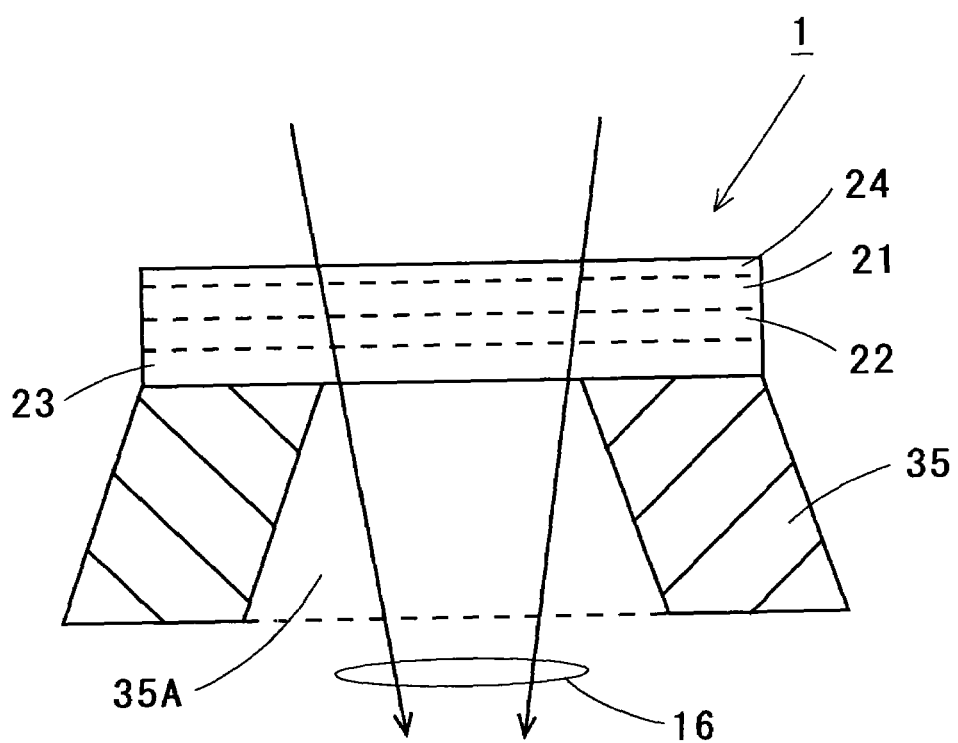
FIG. 6 is a cross sectional diagram illustrating the structure of an X-ray target according to the present invention.

The X-ray target 1 used in this form of implementation may alternatively comprise the X-ray targets 20 and 25. In any case, the X-ray targets 1, 20, 25 is preferably fastened to the upper surface of a support block so that the filmy X-ray targets 1, 20, 25 may be held mechanically against its bending when they are irradiated with the convergent electron beam 16. For example, such a support block 35 as shown in FIG. 6 is in the form of a tubular truncated cone having a hollow 35A passing through its center. The hollow 35A is preset to be larger in size than the size of the convergent electron beam 16 so that the latter may be passed through without hitting on the body of the support block 25. The support block 35 is made of a material that is high in thermal conductivity such as copper to dissipate the heat generated at the X-ray targets 1, 20, 25 when the convergent electron beam 16 is applied thereto. It is designed to cause the heat created at the X-ray target 1 to be transferred to the support block. Further, the support block 35 may be provided internally with piping for cooling (not illustrated). In this case, circulating a coolant such as water through the piping for cooling further enhances the cooling effect.

Figure 7:
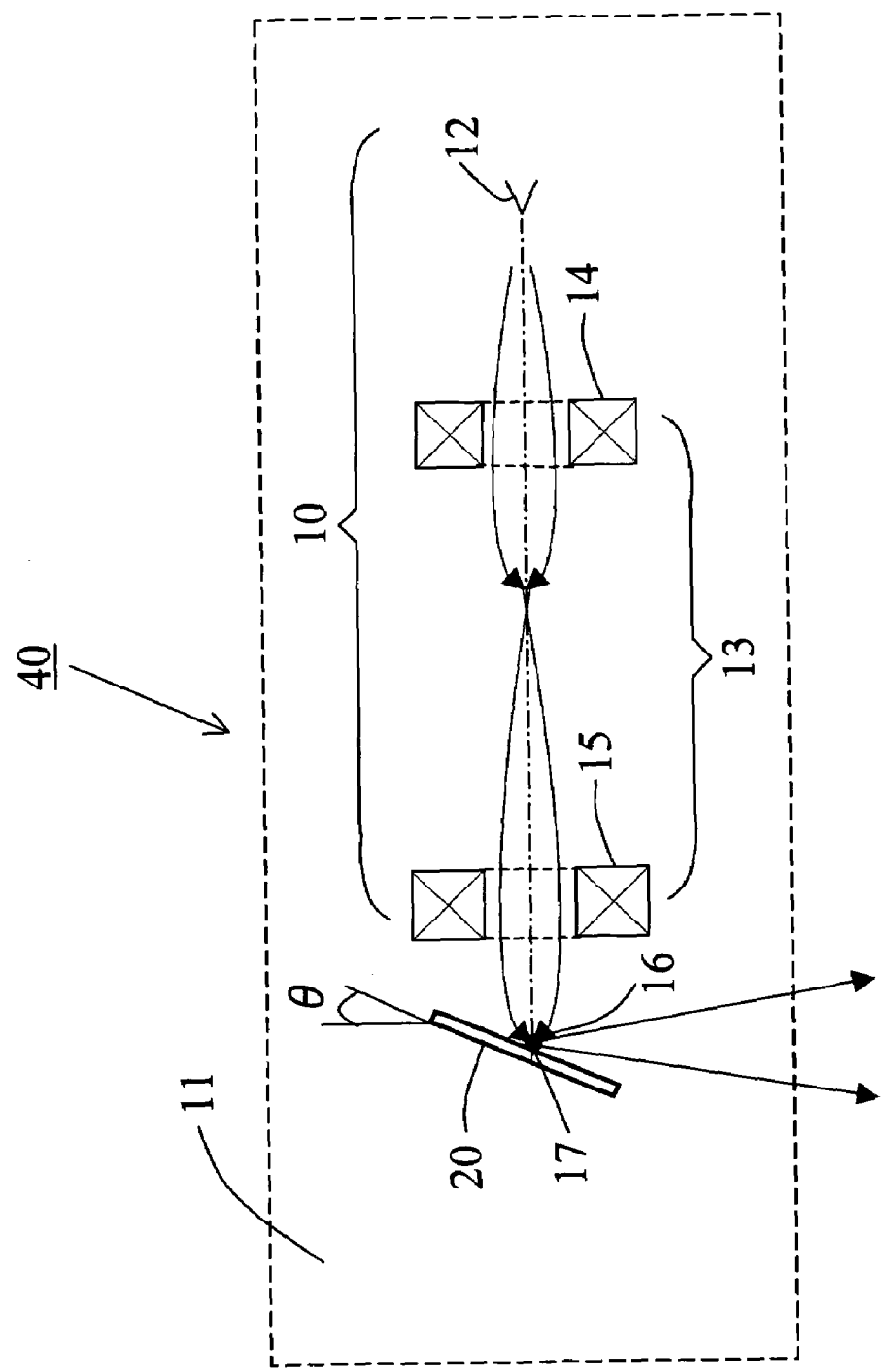
FIG. 7 is a schematic diagram illustrating the construction of a modification of the X-ray apparatus according to the second form of implementation of the present invention.

Mention is next made of a modification of the X-ray apparatus according to the second form of implementation. FIG. 7 is a schematic diagram illustrating the construction of such a modification of the X-ray apparatus according to the second form of implementation. The X-ray apparatus shown in the Figure as designated by reference numeral 40 differs from the X-ray apparatus 30 in that it uses the X-ray target 20 of reflection type as its X-ray target. As this X-ray target is the same in construction as the X-ray target 20 according to the first form of implementation, its repeated explanation is omitted.

For the X-ray targets 1, 20, 25 in the X-ray apparatuses 30, 40, it is preferable to use the structure that a number of target layers are arranged in the form of a matrix as shown in FIG. 4. An individual matrix element may be exchanged by a mechanical operation thereof or changing the position of irradiation with an electron beam and used for a selected time period or the like. Thus, exchanging a target layer 22 and using it for a selected time period or the like eliminates the need to exchange an X-ray targets 1, 20, 25 upon breaking the vacuum of the vacuum chamber 11, thereby enhancing its convenience.

Mention is next made of operations of the X-ray apparatus according to the second form of implementation of the invention.

According to the X-ray targets 1, 20, 25 used in the X-ray apparatuses 30, 40 of the present invention, the accelerated convergent electron beam when passing through the films of the first and second cap layers 21 and 23 made of a light element compound is not much absorbed by it, thus penetrating it while restraining the target layer 22 within the multilayer film structure from being heated. As a result, the intensity of the convergent electron beam 16 can be increased. Therefore, the brightness of the X-ray source can be raised. Further, making the target layer 22 thinner can also make the X-ray source three-dimensionally smaller in focus size.

According the X-ray apparatuses 30, 40, the X-ray emission efficiency can be improved, since the convergent electron beam 16 can be narrowed to the size of the target layer 22 or the target section 26 and its intensity can be raised for application to the X-ray targets 1, 20, 25. As a consequence, it is possible to make the focus size of the electron beam smaller according to the size of the target layer 22 or the target section 26. For example, the focus size can be reduced to the nm order. Therefore, the nano focus X-rays 17 can be obtained.

The Third Form of Implementation

Mention is made of an X-ray microscope using an X-ray generator according to a third form of implementation of the present invention.

Figure 8:
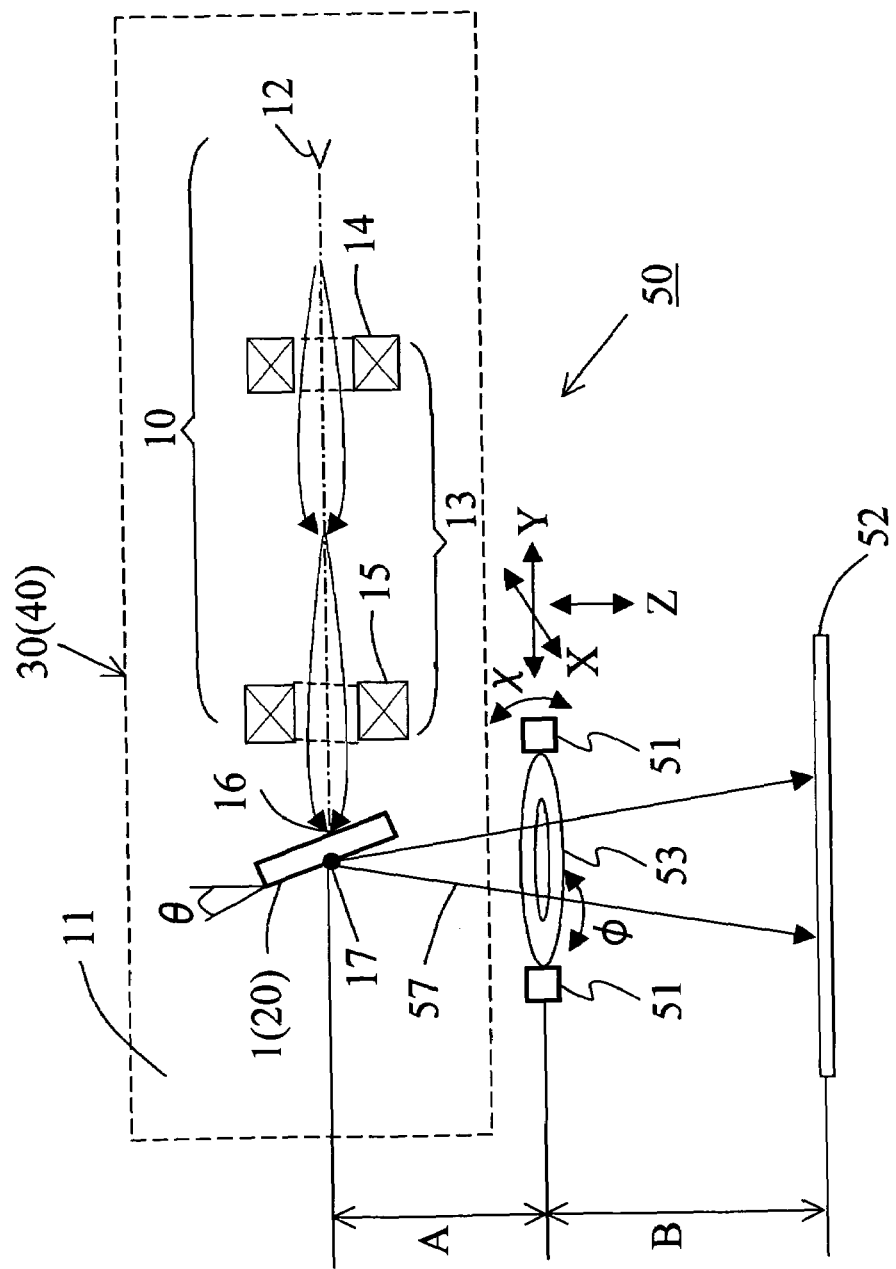
FIG. 8 is a schematic diagram illustrating the construction of an X-ray microscope using an X-ray generator according to a third form of implementation of the present invention.

FIG. 8 is a schematic diagram illustrating the construction of such an X-ray microscope using an X-ray generator. As shown in the Figure, The X-ray microscope 50 according to the present invention comprises the X-ray generator 30, an observational sample holder section 51 and an X-ray detecting means 52. Microfocus X-rays 17 generated from the X-ray generator 30 becomes divergent X-rays 57 and are detected as an image at the X-ray detecting means 52.

The observational sample holder section 51 may be equipped with stages for freely adjusting X-, Y- and Z-axis movements, rotation ($\phi$) of the X-Y plane and angle ($\chi$). The X-ray generator 30 may replace the X-ray generator 40.

The X-ray detecting means 52 can use an X-ray film, an imaging plate or an image sensor such as CCDs. If the X-ray detecting means 52 comprises an image sensor such as CCDs, the same can further be furnished with an image processing means. This image processing means can process signals from CCDs, display on a display device and tint a contrast by a phase contrast or absorption method to be described later.

Mention is next made of operations of the X-ray microscope according to the present invention. The microfocus X-ray source 17 provides divergent X-rays 57, which then make an image. Here, assuming that the distance between the microfocus X-ray source 17 and an object to be observed 53 is A and that the distance between the object 53 and the X-ray detecting means 52 is B, then the magnification m becomes $m=(A+B)/A$. The magnification can be adjusted by change of the intervals of A and B. Such an adjustment may be made by moving the observational sample holder section 51 up and down along the Z-axis.

It follows therefore that having the X-ray source with a micro focus size of several nm, the X-ray microscope of the present invention can have its resolution reduced to such a reduced focus size, though depending upon the resolution of the X-ray detecting means 52. Consequently, when using a two-dimensional image sensor as the X-ray detecting means 52, it is preferable to select a pixel number therefor commensurate with the resolution. The X-ray microscope of the present invention, using X-rays having a micro focus size of several nm and high intensity, makes it possible to readily obtain a resolution of several nm. Further, an observable object image can be obtained with a contrast by both absorption and phase contrast of the object.

Figure 9:
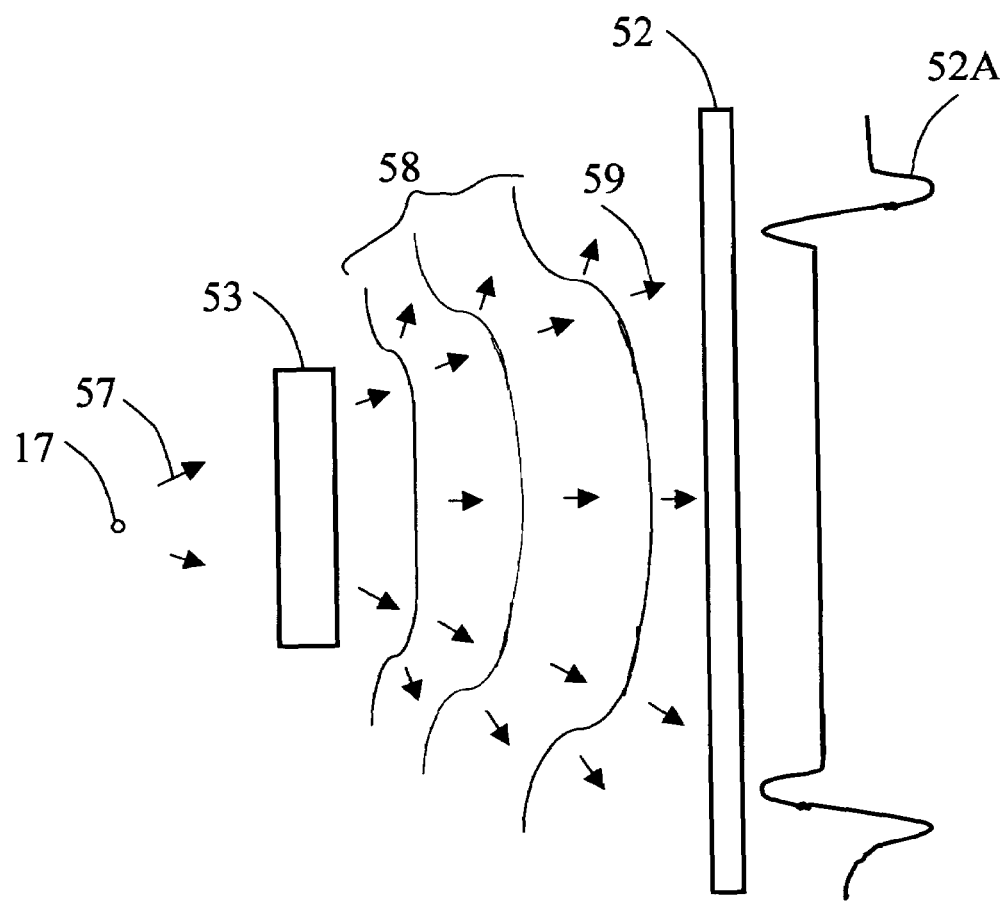
FIG. 9 is a diagram schematically illustrating a contrast by phase difference.

FIG. 9 is a diagram schematically illustrating a contrast by phase contrast or phase differences. Incident divergent X-rays 57 emitted from the microfocus X-ray source 17 penetrate the observable object 53 and are caused to have their phases varied by changes in density and changes in external form of the object, creating their wave surfaces 58. And, X-ray photons 59 advance in directions perpendicular to the wave surfaces 58 and are incident upon the X-ray detecting means 52 to form an image 52A. In the Figure, the contrast of the image 52A is shown to be created at an edge of the observable object 53. According to the X-ray microscope 50 of the present invention, an image is obtained that is due to both X-ray absorption and phase contrast.

If the X-ray detecting means 52 is an image sensor such as CCDs and is provided further with an image processing means, then the image can be processed with a view taken of its contrast intensity.

Using the X-ray microscope to irradiate a living body as the observable object 53 with microfocus X-rays while utilizing the phase contrast makes it possible to obtain an X-ray image that can depict in detail hairs and blood vessels of, e.g., an insect while simultaneously expressing the three-dimensional shape of an eyeball thereof.

Although this is an example of a living body as the observable object 53, the X-ray microscope according to the third form of implementation can be applied to other than living bodies and to a structure such a semiconductor element, a very large scale integrated circuit and a nano structure for their nondestructive inspections and analyses.

Fourth Form of Implementation

Figure 10:
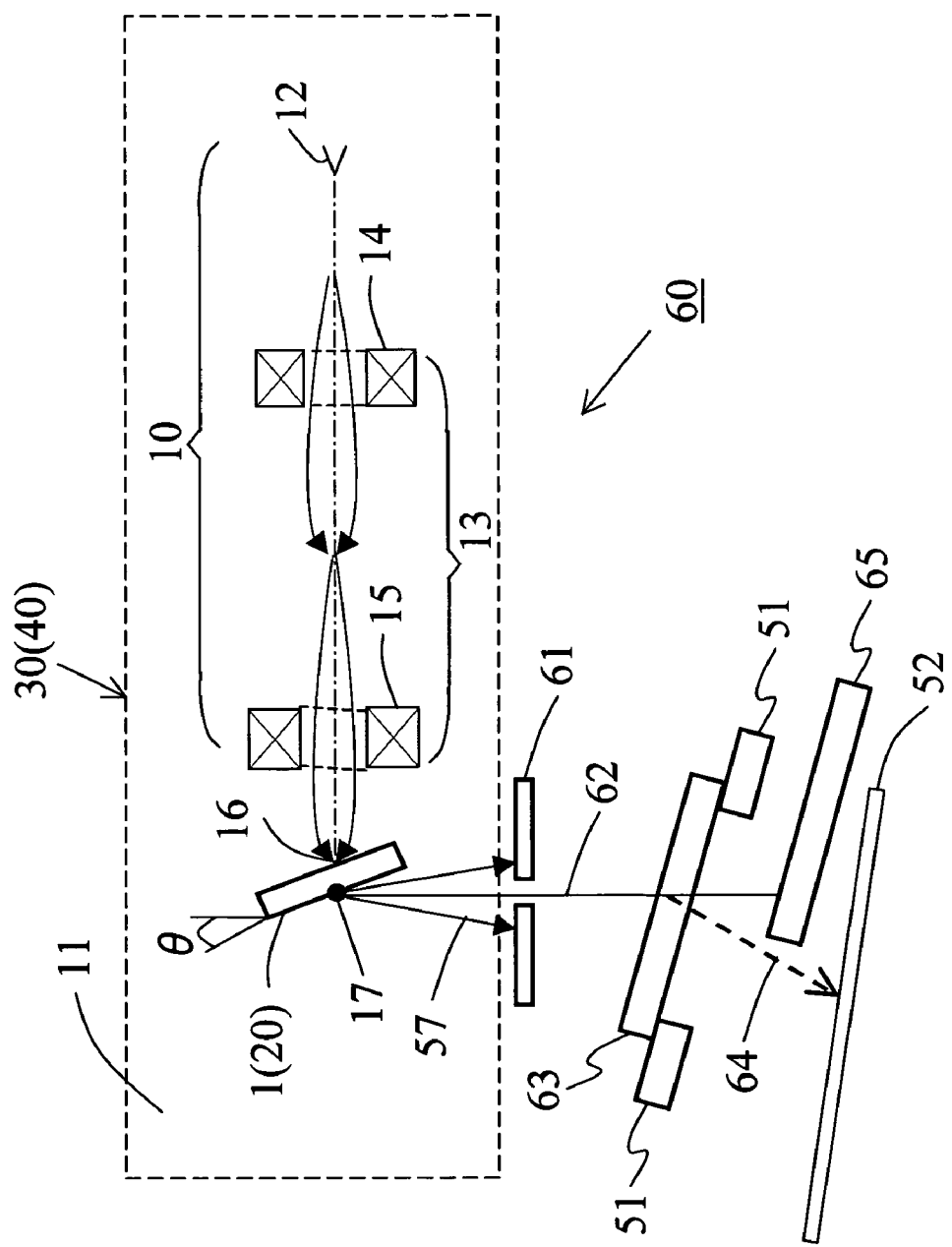
FIG. 10 is a schematic diagram illustrating the construction of an X-ray diffraction apparatus according to a fourth form of implementation.

Mention is made of an X-ray diffraction apparatus according to a fourth form of implementation of the present invention. FIG. 10 is a schematic diagram illustrating the construction of such an X-ray diffraction apparatus according to the fourth form of implementation of the present invention. The X-ray diffraction apparatus 60 of the present invention comprises an X-ray generator 30, an observational sample holder section 51 and an X-ray detecting means 52. Microfocus X-rays 17 generated from the X-ray generator 30 are diffracted through a slit 61 to form only characteristic X-rays 62 desired to be incident onto an observable object 63 such as a single crystal. The slit 61 may be an X-ray optical element for selecting X-rays of a particular wavelength. Such an X-ray optical element comprises an optical element such as a spectrometer (monochromator) or a mirror or a combination of them. The observable object can efficiently be irradiated only with a characteristic wavelength component of microfocus X-rays 17 generated from the X-ray generator 30. And, diffracted X-rays 64 from the observable object 63 are detected at the X-ray detecting means 52. The X-ray detecting means 52 may use such as an X-ray film or imaging plate. Then, so that only diffracted X-rays 64 make an image and so as to prevent the X-rays 62 which are not diffracted but going straight on from being incident on the X-ray film 52, there is provided a douser 65.

The observational sample holder section 51 may be provided with stages capable of freely adjusting the movements in the directions of X-, Y- and Z-axes for the observable object 63, the rotation (φ) of the X-Y plane and the angle (χ). Effecting a translational scanning movement of this observational sample holder section 51 together with the X-ray detecting means 52 allows an X-ray diffraction image in a plane of the observable object 63 to be obtained. The X-ray generator 30 may alternatively use the X-ray generator 40.

According to the X-ray diffraction apparatus of the present invention that uses the X-ray generator with the X-ray source of a micro focus size of several nm and high intensity, an X-ray diffraction image of a very small area can easily be obtained.

Fifth Form of Implementation

Figure 11:
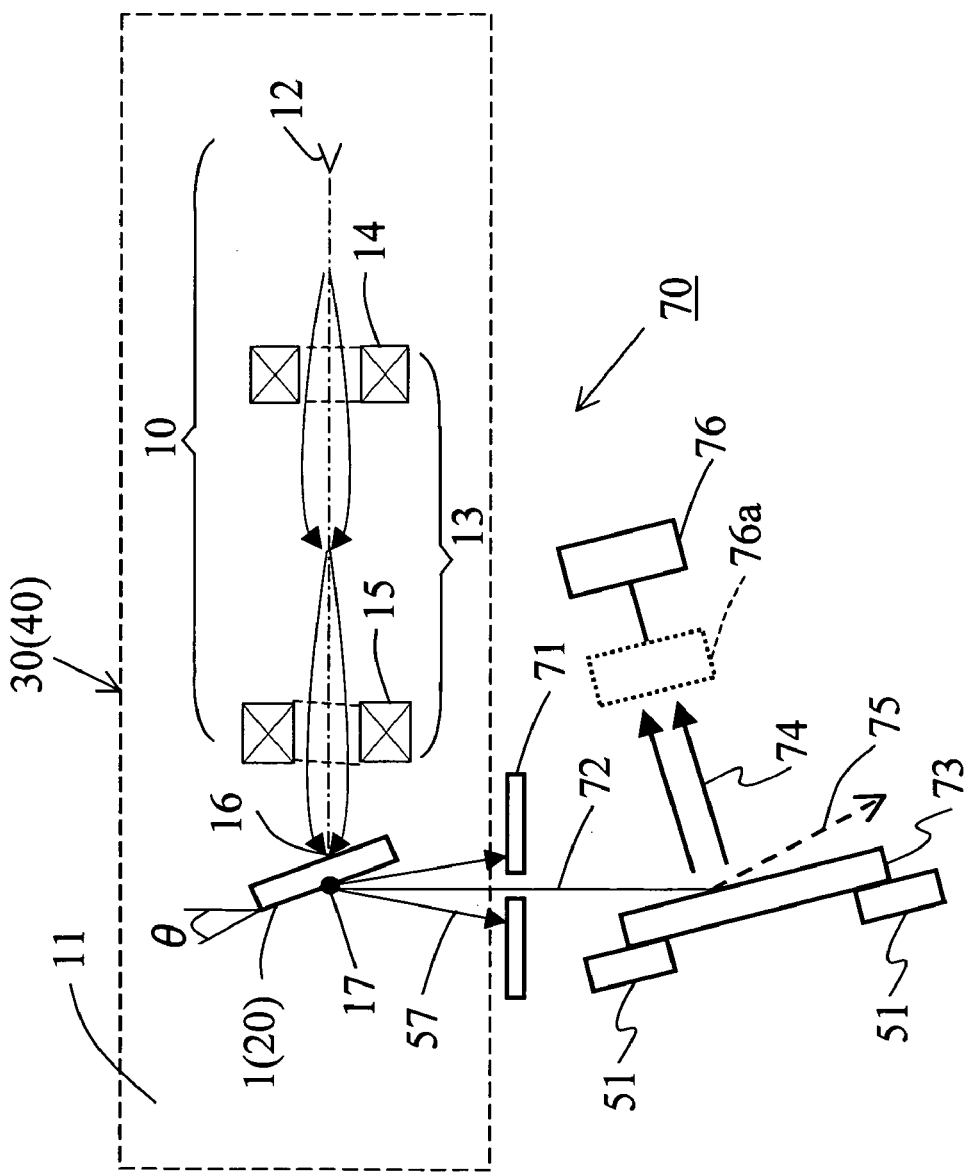
FIG. 11 is a schematic diagram illustrating the construction of an X-ray fluorescence analysis apparatus according to a fifth form of implementation.
Figure 12:
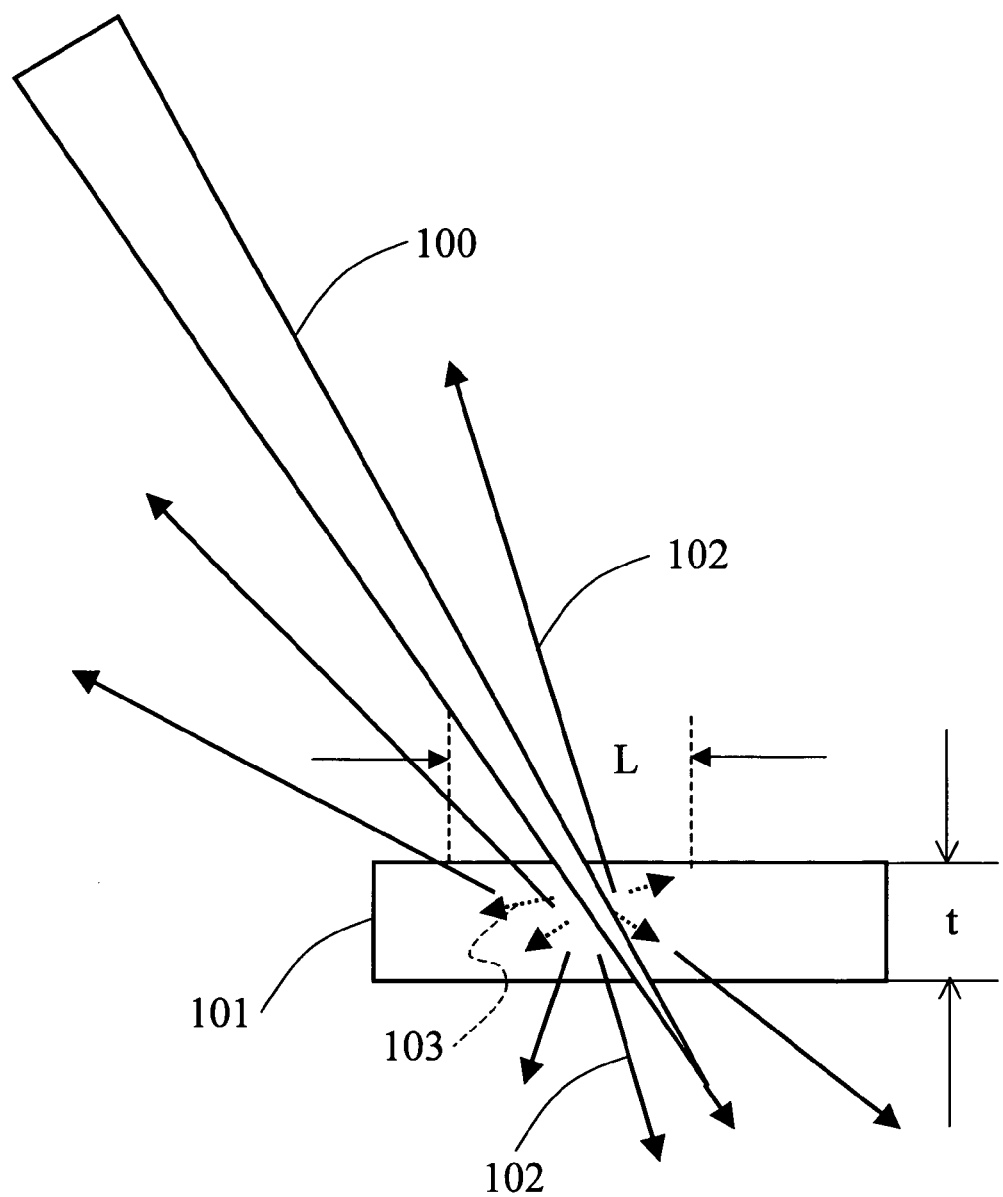
FIG. 12 is a diagram schematically illustrating a conventional X-ray source.

Mention is made of a fluorescent X-ray analysis apparatus according to a fifth form of implementation of the present invention. FIG. 11 is a schematic diagram illustrating the construction of such a fluorescent X-ray analysis apparatus according to the fifth form of implementation of the present invention. As shown in the Figure, the fluorescent X-ray analysis apparatus 70 comprises an X-ray generator 30, an observational sample holder section 51 and an X-ray detecting means 76. Microfocus X-rays 17 generated from the X-ray generator 30 are diffracted through a slit 71 to form only characteristic X-rays 72 desired to be incident on an observable object 73 where fluorescent X-rays 74 and reflected X-rays 75 are generated. The slit 71 may be an X-ray optical element for selecting X-rays of a particular wavelength. Such an X-ray optical element comprises an optical element such as a spectrometer (monochromator) or a mirror or a combination of them. And, fluorescent X-rays 74 from the observable object 73 are detected by the X-ray detecting means 76. The X-ray detecting means 76 may use a scintillation detector including a spectrometer 76a for the analysis of X-ray wavelengths. It may alternatively be a gas flow proportional counter, or an energy dispersive semiconductor detector. In particular, with an energy dispersive semiconductor detector, the spectrometer 76a is unnecessary.

The observational sample holder section 51 may be provided with stages capable of freely adjusting the movements in the directions of X-, Y- and Z-axes, the rotation (φ) of the X-Y plane and the angle (χ). Effecting a translational scanning movement of this observational sample holder section 51 together with the X-ray detecting means 76 allows a fluorescent X-ray distribution in a plane of the observable object 73 to be obtained. Further, the X-ray generator 30 may alternatively use the X-ray generator 40.

According to the fluorescent X-ray analysis apparatus of the present invention that uses the X-ray generator with the X-ray source of a micro focus size of several nm and high intensity, the fluorescent X-ray analysis of a very small area can easily be made.

As mentioned in the foregoing, according to the X-ray microscope using the X-ray generator of the present invention, the transmission image of an observable object which cannot be obtained with an optical microscope by visible light, a SEM, a scanning tunneling microscope or an atomic force microscope in a surface height image can be observed with high resolution.

Also, according to the X-ray diffraction apparatus using the X-ray generator of the present invention, diffraction X-ray images can be obtained of very small areas of various observable objects.

Further, according to the fluorescent X-ray analysis apparatus using an X-ray generator of the present invention, the fluorescent X-ray analysis can be made of a very small area of one of various observable objects.

It is needless to say that the invention is not intended to be limited to the specific embodiments thereof set forth above, but to include all possible embodiments that can be made within the scope with respect to the features specifically set forth in the appended claims.

INDUSTRIAL APPLICABILITY

According to an X-ray target of the present invention, it is possible to provide an X-ray target capable of generating highly intense X-rays having a micro focus size in an nm order. According to an X-ray generator of the invention, it is possible to generate X-rays which are highly intense and have a micro focus size in an nm order. According to an X-ray diffraction apparatus of the present invention, it is possible to measure the X-ray diffraction of a very small area with a highly intense and microfocus X-ray source. According to a fluorescent X-ray analysis apparatus of the invention, it is possible to make the fluorescent X-ray analysis of a very small area with a highly intense and microfocus X-ray source. Further, according to an X-ray microscope of the present invention, it is possible to provide a microscope with a high resolution of several nm that has never been achieved heretofore and to obtain a contrast image by phase contrast together with a conventional image by absorption.

What is claimed is:

1. An X-ray target, comprising:
a first cap layer;
a target layer composed of a material capable of generating characteristic X-rays, said target layer formed under said first cap layer; and
a second cap layer formed under said target layer; and
a support block formed under said second cap layer to hold said structure, wherein a first material of which said first and second cap layers are composed is lower in electron beam absorptivity than a second material of which said target layer is composed, said target layer is buried and arranged in the form of a linear or an elliptical matrix in said first and the second cap layer, and each target layer of said matrix is made a microfocus X-ray source corresponding to its size.

2. The X-ray target as set forth in claim 1, wherein said target layer is composed of a material capable of generating characteristic X-rays of a wavelength ranging between 0.3 and 10 Å.

3. The X-ray target as set forth in claim 1, wherein said first and second cap layers are composed of a material selected from the group which consists of B, C, SiC and $B_4C$.

4. The X-ray target as set forth in claim 1, wherein said target layers are of an identical size.

5. The X-ray target as set forth in claim 1, wherein said target layers are varied in size.

6. The X-ray target as set forth in claim 1, wherein on the first cap layer is provided an antistatic layer.

7. An X-ray apparatus comprising:
an X-ray source made of an electron beam generating section and
an X-ray target, wherein said X-ray target comprises
a first cap layer,
a target layer, and
a second cap layer, wherein said first cap layer, said target layer, and said second cap layer are successively laminated in the recited order, thereby forming a laminated structure, and
a support block to hold said laminated structure, wherein said first and second cap layers are composed of a first material which is lower in electron beam absorptivity than a second material of which said target layer is composed, said target layer is buried and arranged in the form of a linear or an elliptical matrix in said first and second cap layers, and each target layer of the matrix forms a microfocus X-ray source corresponding to its size, wherein each target of said matrix is irradiated with a convergent electron beam generated by said electron beam generating section to cause said target to generate a microfocus X-rays.

8. The X-ray apparatus as set forth in claim 7, wherein said electron beam generating section comprises an electronic lens, said X-ray target is disposed with an inclination to the convergent electron beam generated by said electron beam generating section, and said convergent electron beam is similar in shape and size to each target layer of said matrix.

9. The X-ray apparatus as set forth in claim 7, wherein on said first cap layer is provided an antistatic layer.

10. The X-ray apparatus as set forth in claim 7, wherein said X-ray apparatus is an X-ray diffraction apparatus further provided with an observation sample holder section and an X-ray detecting means.

11. The X-ray apparatus as set forth in claim 7, wherein said X-ray apparatus is a fluorescent X-ray analysis apparatus further provided with an observation sample holder section and an X-ray detecting means.

12. The X-ray apparatus as set forth in claim 7, wherein said X-ray apparatus is further provided with an X-ray optical element.

13. An X-ray microscope comprising:
an electron beam generating section,
an X-ray target,
an observation sample holder section for an observable object, and an X-ray detecting means,
wherein said X-ray target comprises:
a first cap layer,
a target layer, and
a second cap layer, wherein said first cap layer, said target layer, and said second cap layer are successively laminated in the recited order, thereby forming a laminated structure,
wherein said first and second cap layers are composed of a material which is lower in electron beam absorptivity than that of which said target layer is composed,
wherein said X-ray target is irradiated with a convergent electron beam generated by said electron beam generating section to cause said target to generate microfocus X-rays, and said microfocus X-rays are used as divergent X-rays to obtain a transmission X-ray image of said observable object.

14. The X-ray microscope as set forth in claim 13, wherein said electron beam generating section includes an electronic lens, said X-ray target is disposed with an inclination to the convergent electron beam generated by said electron beam generating section, and said convergent electron beam is similar in shape and size to each target layer of the matrix of the X-ray target.

15. The X-ray microscope as set forth in claim 13, wherein on said first cap layer is provided an antistatic layer.

16. The X-ray microscope as set forth in claim 13, wherein said transmission X-ray image includes a contrast by phase contrast.

17. The X-ray microscope as set forth in claim 13, wherein said X-ray detecting means is an image sensor and provided with an image processing means for said image sensor, and X-rays are used as divergent X-rays to obtain a transmission X-ray image of said observable object.

\* \* \* \* \*